(12) United States Patent
Sieben

(10) Patent No.: US 6,235,021 B1
(45) Date of Patent: *May 22, 2001

(54) ABLATION SHEATH

(75) Inventor: Wayne Sieben, Alexandria, MN (US)

(73) Assignee: Scimed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/431,584

(22) Filed: May 1, 1995

(51) Int. Cl.$^7$ .................................................. A61B 18/18
(52) U.S. Cl. ............................ 606/41; 606/108; 607/122
(58) Field of Search ..................................... 606/41, 45–50, 606/108; 607/100–102, 104, 115, 116, 119, 122; 128/642; 600/372–374, 585; 604/22

(56) References Cited

U.S. PATENT DOCUMENTS

| | | | |
|---|---|---|---|
| 4,913,142 | * | 4/1990 | Kittrell et al. ............................ 606/7 |
| 4,929,246 | * | 5/1990 | Sinofsky .................................. 606/8 |
| 5,122,138 | * | 6/1992 | Manwaring ............................. 606/46 |
| 5,197,963 | * | 3/1993 | Parins ..................................... 606/46 |
| 5,403,311 | * | 4/1995 | Abele et al. ............................ 606/49 |
| 5,456,694 | * | 10/1995 | Marin et al. .......................... 606/198 |
| 5,471,982 | * | 12/1995 | Edwards et al. ...................... 600/374 |
| 5,487,385 | * | 1/1996 | Avitall .................................. 128/642 |
| 5,487,757 | * | 1/1996 | Truckai et al. ....................... 607/122 |
| 5,500,012 | * | 3/1996 | Brucker et al. ....................... 607/122 |
| 5,507,744 | * | 4/1996 | Tay et al. ............................... 606/50 |
| 5,609,151 | * | 3/1997 | Mulier et al. ......................... 128/642 |
| 5,639,276 | * | 6/1997 | Weinstock et al. ................... 606/129 |
| 5,755,714 | * | 5/1998 | Murphy-Chutorian ................ 606/15 |
| 5,785,706 | * | 7/1998 | Bednarek ................................ 606/41 |
| 6,022,319 | * | 2/2000 | Willard et al. ........................ 600/470 |

* cited by examiner

Primary Examiner—Michael Peffley
(74) Attorney, Agent, or Firm—Henricks, Slavin & Holmes LLP

(57) ABSTRACT

A sheath is provided to introduce electrophysiology catheters into the heart. The sheath has controlled geometric and physical properties and may be used to control ablation therapy.

27 Claims, 3 Drawing Sheets

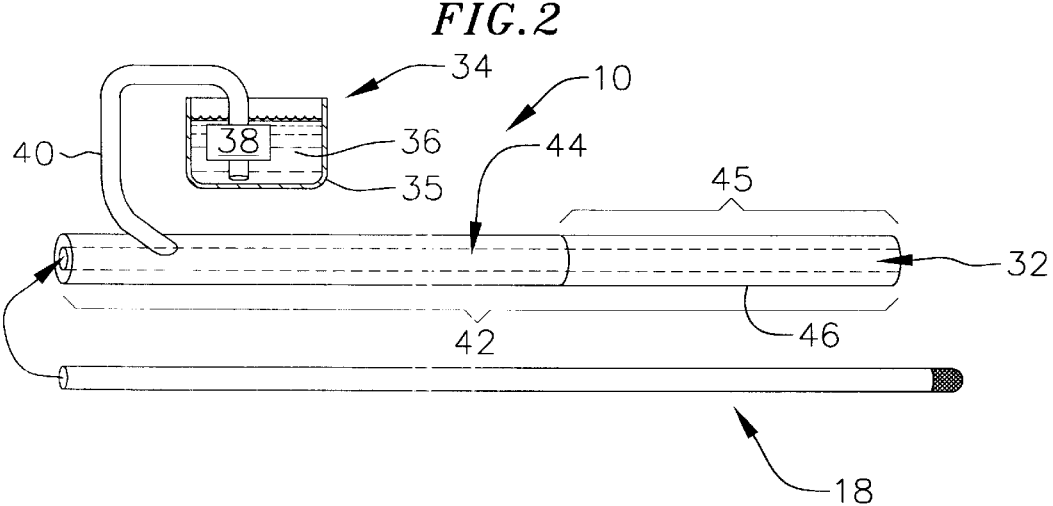
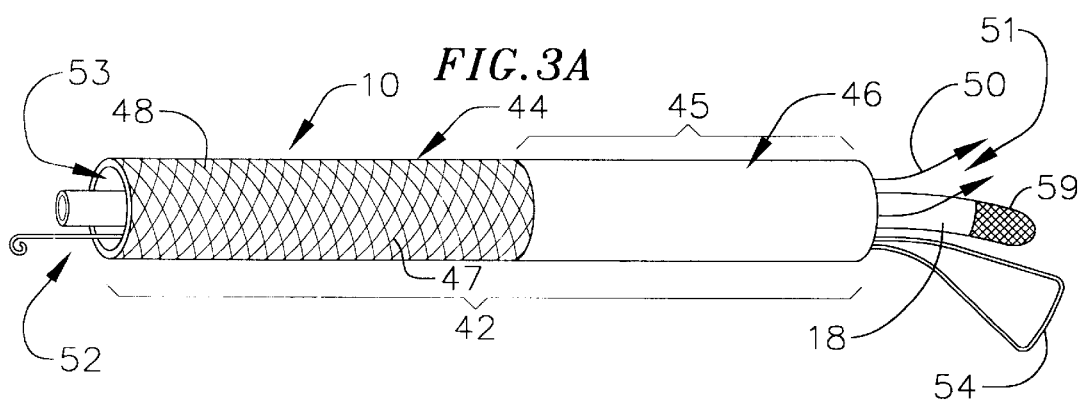
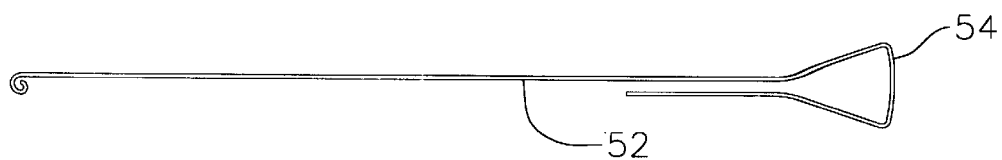

ABLATION SHEATH

FIELD OF THE INVENTION

The present invention relates generally to electrophysiology equipment and more particularly to an apparatus and method for using the apparatus for positioning electrophysiology instruments within the heart of a patient.

BACKGROUND OF THE INVENTION

Electrophysiologic mapping and cardiac ablation are two procedures which are typically performed inside of a beating heart. The mapping procedure is diagnostic and it is intended to reveal the location of regions of ectopic electrical activity within the heart which can give rise to tachyarrhythmias. Once an ectopic site has been localized, it is common to ablate tissue in that region of the heart to prevent conduction of electrical signals in that portion of the cardiac tissue. The ablation of tissue is a therapeutic and has been demonstrated to eliminate some tachyarrythmias.

Both brachial and femoral approaches to the interior of the heart are commonly used to introduce catheters. Approaching the heart through the thorax is not widely employed at the present time. Consequently the ability to quickly and reliably exchange instruments within the heart chamber is desirable. However it is difficult to exchange diagnostic and therapeutic catheters given current therapeutic approaches.

SUMMARY OF THE INVENTION

The present invention includes an over-tube or sheath which is guided into a heart chamber by a steerable catheter. This sheath is left in place in the heart during the procedures and it is used to permit the rapid exchange of diagnostic and therapeutic catheters through the central lumen of the sheath. The physical and mechanical properties as well as the geometry of the sheath are important properties of the device.

In some embodiments of the sheath a lateral window is provided in the distal tip to facilitate the creation of certain types of ablation lesions. Additionally a distal foot member may be used with the sheath. This distal foot may be retracted or articulated to bring therapeutic catheters into contact with the heart wall and to permit the formation of multiple lesions.

BRIEF DESCRIPTION OF THE DRAWINGS

The structures shown in the various figures are illustrative and exemplary and should not be regarded as limiting the form or appearance of the invention. Throughout the several figures identical reference numerals depict identical structure wherein:

FIG. 2 is a schematic diagram of the ablation sheath juxtaposed with an ablation catheter;

FIG. 3A is a schematic diagram of the ablation catheter within the ablation sheath;

FIG. 3B is a schematic diagram of the ablation catheter within the ablation sheath;

DETAILED DESCRIPTION

Figure 1:
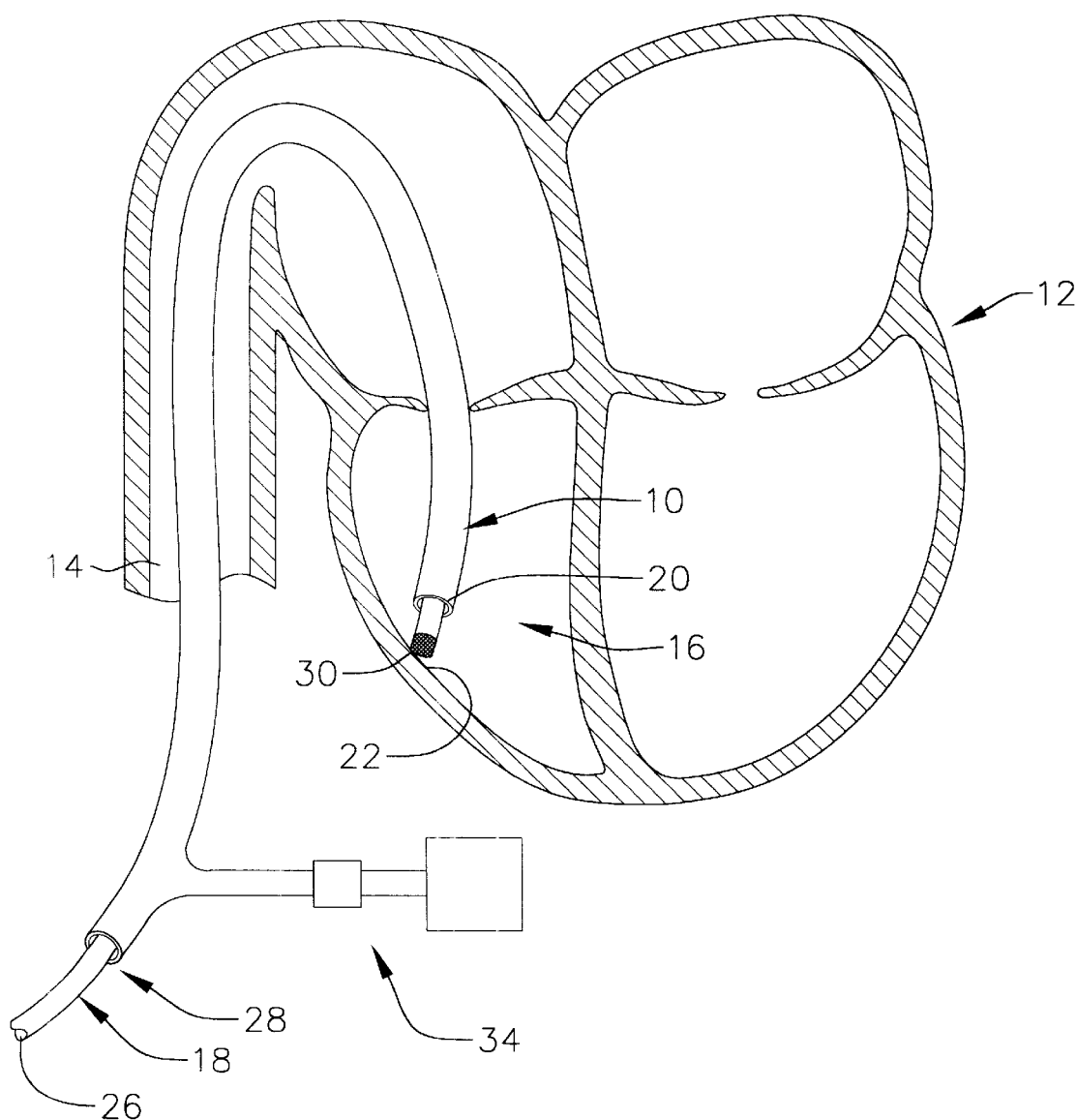
FIG. 1 is a schematic representation of the ablation sheath in use.

FIG. 1 is a schematic view which shows a patient heart 12 in isolation. The ablation sheath 10 has been inserted into a peripheral vessel 14 and advanced into a heart chamber 16 such as a ventricle. In the drawing a companion ablation catheter 18 has been advanced through the ablation sheath 10 and moved into contact with the cardiac tissue at site 22. This drawing shows the proximal end 28 of the ablation sheath 10 located outside the patients body where it may be manipulated by an attending physician. Similarly the proximal end 26 of the ablation catheter 18 is located outside the patients body for manipulation by the attending physician. It is generally preferable to use ablation catheters with a diameter less than about ten French and preferably equal to about seven French. The perfusion apparatus 34 is also coupled to the ablation sheath 10 and operated by the physician. In use the ablation sheath is advanced into position in the heart by advancing the ablation sheath over a steerable catheter. In this context the term steerable requires both deflectability and torqueability. It is expected that an ablation catheter will be used for this portion of the procedure however alternative catheter structures may be used.

FIG. 2 shows the companion ablation catheter 18 withdrawn from the central lumen 32 of the ablation sheath 10. This figure also shows the illustrative perfusion apparatus 34 in more detail. The perfusion apparatus 34 includes a reservoir 35, along with a suitable pump 38 and tubing 40. When used for therapeutic ablation it is expected that the physician will want to perfuse the central lumen 32 of the ablation sheath 10 with a fluid 36 such as normal saline (NaCl) or the like. As seen in the figure the reservoir 35 holds the perfusion fluid 36 and is coupled to a suitable pump 38 which supplies the solution though suitable tubing 40 connected to the central lumen 32 through an off-axis sidearm.

In FIG. 3 the total length of the ablation sheath 10 is shown in the diagram by length 42. In general, the ablation sheath will be one meter in length, or longer. The body 44 of the sheath is divided into two distinct regions, which are shown in the figure as distal tip portion 46 and proximal body section 48.

In all embodiments the distal tip portion 46 will be short and on the order of two to nine inches depicted in the FIG. 2 by length 45. For lengths shorter than about nine inches it is critical that this distal tip portion 46 be substantially more flexible than the proximal body section 48. Typically, the proximal body section 48 will include a woven reinforcing braid which permits the structure to transmit torque, which is important for guiding and positioning the ablation sheath 10 within the patient's heart. The distal tip section should exhibit a moment (or stiffness) "E*I", which is less than 0.2 lbs-inch squared. Although any of a variety of materials can be utilized to fabricate both the proximal section 48 and the distal tip portion 46, it is preferred to have the outer body diameter constant throughout the length of the ablation sheath 10. It is also considered advantageous to have a constant diameter inner central lumen 32. To achieve the required variation in stiffness, it is preferred to adopt a material such as Pebax (a nylon-acetal material) for the distal tip portion 46 and to reinforce this material with a fabric represented in the figure by fibers typified by fiber 47, for the proximal section 48.

As shown in FIG. 2, saline solution can emerge from the intersticial area 52 between the ablation catheter 18 and the distal opening 51 of the ablation sheath 10. This on-axis distal opening 51 is indicated in the figure near the flow arrow 50 which illustrates fluid flow through the intersticial area 52. It is preferred to have the distal opening have a circular cross section.

As seen in FIG. 3A it may be useful to insert a incremental motion catheter 52 into the central lumen 32 the ablation sheath 10. It should be appreciated that an additional lumen dedicated to this incremental motion catheter is contemplated as well. This incremental motion catheter 52 may take the form of a 0.010 inch diameter wire which includes a blunt distal loop 54, which forms a foot member that can be urged into position against cardiac tissue to control the motion of the ablation catheter 18 and ablation sheath 10 by sequentially advancing and retracting the incremental motion catheter 52 in and out of the sheath opening 51. The tip of the ablation catheter 18 may be reliably and accurately moved along a cardiac surface by manipulating the deflectable ablation catheter in conjunction with incremental motion catheter 52.

FIG. 3B shows the companion incremental motion catheter 52 in isolation juxtaposed to the ablation sheath 10, which includes a ablation catheter 18 and a incremental motion catheter 52 in the operating position. Depending on the particular section of the heart to be ablated, the incremental motion catheter 52 may take various shapes and may be made of plastically deformable material such as stainless steel to facilitate reshaping.

Figure 4:
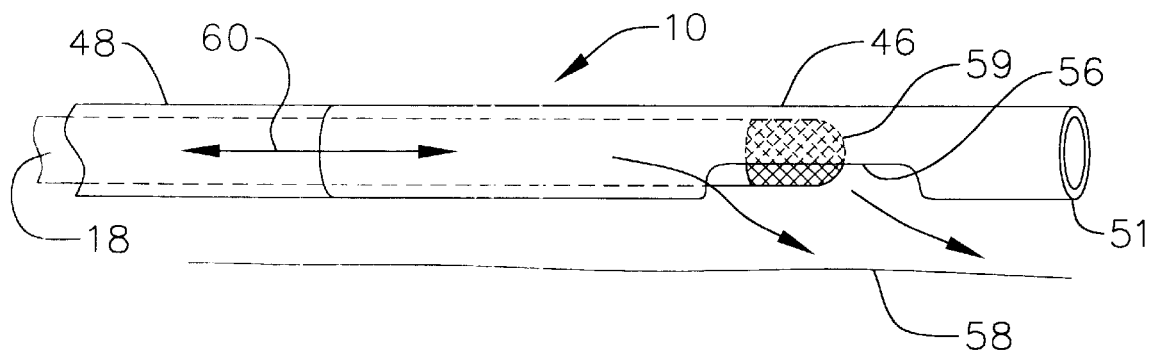
FIG. 4 is schematic diagram of an alternate embodiment of the ablation sheath proximate cardiac tissue.

FIG. 4 represents an alternate embodiment of the ablation sheath 10, with a lateral window 56 positioned in the distal tip portion 46 of the ablation sheath body. This lateral window is cut into the side wall of the sheath so that an opening is formed which communicates with the central lumen 32. In use, the lateral window directs the flow of saline fluid toward the cardiac tissue 58. This window 56 also occludes or masks the electrode 59 at the distal tip of the ablation catheter 18. By occluding the electrode and flooding it with saline the size of the lesion produced in the cardiac tissue 58 can be controlled. The ability to occlude a segment of the ablation catheter electrode by relative motion between the catheter and the ablation sheath 10, as indicated by arrow 60, is an important feature permitting the physician to control the therapy supplied through the ablation sheath 10.

Figure 5A:
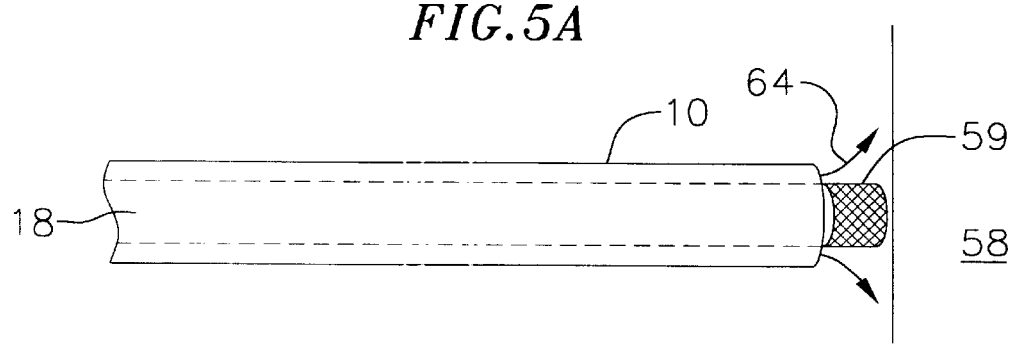
FIG. 5A is a schematic diagram showing relative sheath and electrode locations for ablation.
Figure 5B:
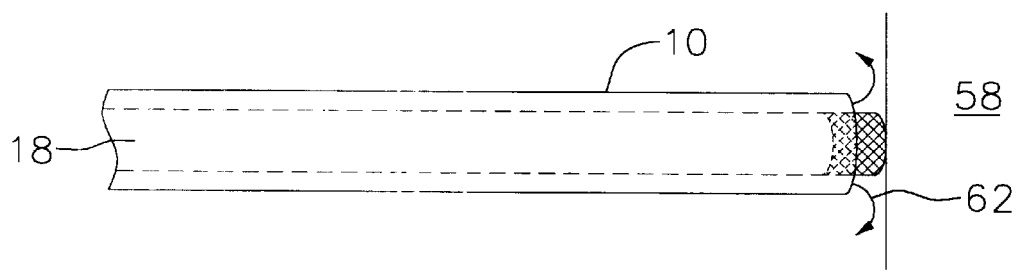
FIG. 5B is a schematic diagram showing relative sheath and electrode locations for ablation.

FIG. 5 includes several panels represents the use of the sheath in several configurations against a segment of cardiac tissue 58. In this instance, the sheath has been steered and guided to have nearly perpendicular abutment with the interior surface of the heart wall. In panel A, the sheath has been retracted to permit the maximum flow of saline past the ablation electrode 59, as indicated by flow arrow 64. In panel B, sheath 10 has been abutted directly against the cardiac tissue 58, and only a modest flow of saline indicated by flow arrow 62 can emerge from the sheath. In this instance, the fluid is primarily used to cool the electrode, where in panel A, the fluid flow is sufficiently removed from the electrode, and its primary function is to flood the ablation sight to exclude blood from the electrode surface. In panel C, the distal tip portion 46 has been abutted against the cardiac tissue 58, and the ablation electrode 59 has been withdrawn several millimeters from the tissue by relative motion along path arrow 66. In this instance, the saline solution within the distal volume of central lumen 32 acts as the electrode conducting radio frequency ablation emerging directly from the electrode to the cardiac tissue 58. In this fashion, the sheath in combination with an ablation electrode can be used to ablate tissue by contact with a metallic electrode, as shown in panel B, or saline electrode, as shown in panel C. In a similar fashion, the metal electrode can be cooled by the saline, or saline can be used to exclude blood from the ablation sight, as seen in panel A.

Figure 5C:
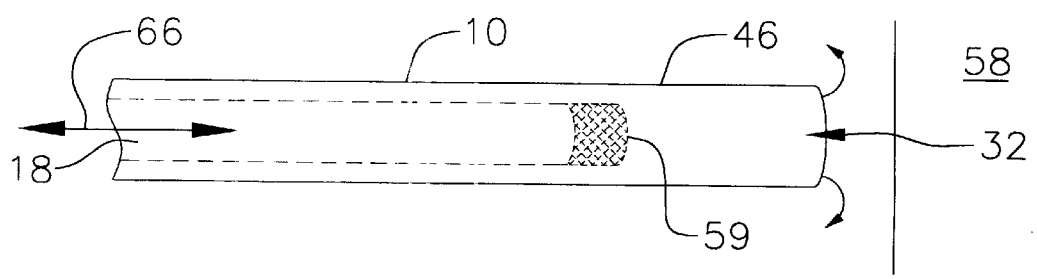
FIG. 5C is a schematic diagram showing relative sheath and electrode locations for ablation.

The demands of the sheath, presented by panel FIG. 5C, are at odds with other criteria for the sheath. However, it has been found that the ablation sheath 10 operates optimally in a critical fashion with stiffness values below 0.2 lbs-inch squared.

The preferred method of performing a measurement to determine the distal stiffness of the ablation sheath maybe determined by supporting a section of the sheath of length L from a cantilever support, and applying a small weight (1.07 grams) to the distal tip. In this instance, a deflection from approximately 1.1 ⅛ millimeters should occur for a length of L=39 millimeters. Stiffness may be computed from this arrangement through the expression $EI=W.L^3/3*D$. Measurements of this type are difficult to make, since the thinness of the tubing can cause it to buckle. Consequently, measurements need to be made with weights, selected such that the deflection angle is less than 3°. The measurements made during the course of developing exemplary versions of the catheter have an accuracy of approximately plus, or minus 5%. Although the preferred sheath construction includes a distal segment with reduced stiffness, as compared to the body section, there are a number of mechanisms which be used to achieve this result. The preferred method is to introduce reinforcing structure in the proximal body section to improve its "torque ability". However, material selection alone can be used to control the relative stiffness. Additionally, it should be recognized that both tapered lumens and tapered outer sheath diameters can also be utilized to provide the relative change in stiffness.

Although the invention has been described in connection with the preferred embodiment, and certain variations on the preferred embodiment, it should be recognized that alternate geometries and structures can be used to carry out the invention.

What is claimed is:

1. A sheath system for use with an ablation catheter defining a predetermined size, the sheath system comprising:

an elongate sheath body defining an ablation catheter lumen, a proximal end, a distal end, a distal end opening of greater size than the ablation catheter, and a proximal end opening, and incremental motion means, including a distal end adapted to extend outwardly from the distal end opening of the sheath body and a proximal end extending outwardly from the proximal end opening of the sheath body and defining a distal portion longitudinal axis, for engaging patient tissue when the distal end opening faces the tissue and moving the sheath in a direction substantially perpendicular to the distal portion longitudinal axis when the distal end opening faces the tissue.

2. A sheath system as claimed in claim 1, wherein the incremental motion catheter defines a substantially flat distal end.

3. A sheath system as claimed in claim 1, wherein the incremental motion means comprises an incremental motion catheter.

4. A sheath system as claimed in claim 3, wherein the distal end of the incremental motion catheter extends outwardly from the distal end of the sheath body.

5. A sheath system as claimed in claim 3, wherein the sheath body defines an incremental motion catheter lumen and the incremental motion catheter is located within the incremental motion catheter lumen.

6. A sheath system as claimed in claim 3, wherein the incremental motion catheter is located within the ablation catheter lumen.

7. A sheath system as claimed in claim 3, wherein the incremental motion catheter defines a closed distal loop.

8. A sheath system as claimed in claim 3, wherein the incremental motion catheter is adapted to move longitudinally relative to the sheath body.

9. A sheath system as claimed in claim 1, wherein the sheath body defines a distal portion extending proximally from the distal end and a proximal portion extending distally from the proximal end, and the distal portion is more flexible than the proximal portion.

10. A sheath system as claimed in claim 1, wherein the sheath body defines a distal portion extending proximally from the distal end and the distal portion defines a stiffness less than 0.2 lbs-inch squared.

11. A sheath system as claimed in claim 1, wherein the incremental motion means is free of any protuberances adapted to engage the ablation catheter.

12. A sheath system as claimed in claim 1, wherein the distal end of the incremental motion means includes a blunt surface extending generally perpendicular to the distal portion longitudinal axis.

13. A sheath system as claimed in claim 12, wherein the blunt surface comprises a flat surface.

14. An electrophysiology system, comprising:

an ablation catheter defining a distal end;

an elongate sheath body defining an ablation catheter lumen, a proximal end, a distal end and a distal end opening of sufficient size to allow the ablation catheter to pass therethrough; and an incremental motion catheter, which is not located within the entire ablation catheter or connected to the distal end of the ablation catheter, defines a longitudinal axis and includes a distal end having a blunt surface extending generally perpendicular to the longitudinal axis, adapted to extend outwardly from the distal end opening of the sheath body and engage patient tissue and a proximal end associated with the proximal end of the sheath body.

15. An electrophysiology system as claimed in claim 14, wherein the elongate sheath body defines a proximal end opening and the incremental motion catheter extends outwardly from the proximal end opening.

16. A sheath system as claimed in claim 14, wherein the sheath body defines an incremental motion catheter lumen and the incremental motion catheter is located within the incremental motion catheter lumen.

17. A sheath system as claimed in claim 14, wherein the incremental motion catheter is located within the ablation catheter lumen.

18. A sheath system as claimed in claim 14, wherein the incremental motion catheter defines a closed distal loop.

19. A sheath system as claimed in claim 14, wherein the incremental motion catheter is adapted to move longitudinally relative to the sheath body.

20. An electrophysiology system as claimed in claim 14, wherein the blunt surface defines a first width, the majority of the incremental motion catheter defines a second width and the first width is greater than the second width.

21. An electrophysiology system as claimed in claim 14, wherein the blunt surface comprises a flat surface.

22. An electrophysiology system for use with a heart chamber, comprising:

an elongate sheath body defining a proximal end, a distal end for insertion into the heart chamber having a stiffness less than 0.2 lbs-inch squared, and a longitudinal axis, the sheath body having a central lumen extending to the distal end, thereby defining a distal end opening, and a window located in spaced relation to the distal end; and an ablation catheter having a distal end and a proximal end, said distal end having an electrode located thereon, said catheter being positioned within said lumen and movable along the longitudinal axis between a first ablating position whereby the distal end of the catheter is substantially aligned with the window and a second ablating position whereby the distal end of the catheter extends at least partially through the distal end opening.

23. The electrophysiology system of claim 22 wherein said ablation catheter and said central lumen define an interstitial area therebetween and said proximal end of said elongate sheath body includes a perfusion apparatus for inducting a perfusion fluid into the interstitial area between said ablation catheter and said central lumen.

24. An electrophysiology system, comprising:

an elongate sheath body defining an ablation catheter lumen, a proximal end, a distal end having an opening, a longitudinal axis and a side opening longitudinally spaced from the distal end opening, and an ablation catheter defining a distal portion having an electrode located thereon and a proximal end, the catheter being positioned within the ablation catheter lumen such that the catheter can move longitudinally relative to the sheath body between a first ablating position where the electrode is substantially aligned with side opening and a second ablating position where the electrode extends at least partially through the distal end opening.

25. A system as claimed in claim 24, wherein the ablation catheter defines a longitudinal axis and the elongate sheath body and ablation catheter are coaxial.

26. A system as claimed in claim 24, further comprising:

an incremental motion catheter including a distal end adapted to extend outwardly from the distal end of the sheath body and engage patient tissue and a proximal end associated with the proximal end of the sheath body.

27. A system as claimed in claim 24, wherein the ablation catheter and the sheath body define a space therebetween, the system further comprising:

perfusion means for supplying saline through the space between the ablation catheter to the distal end opening of the sheath body.

* * * * *